(12) United States Patent
O'Hara et al.

(10) Patent No.: US 7,878,651 B2
(45) Date of Patent: Feb. 1, 2011

(54) REFRACTIVE PRESCRIPTION USING OPTICAL COHERENCE TOMOGRAPHY

(75) Inventors: Keith E. O'Hara, Livermore, CA (US); Scott A. Meyer, Livermore, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 85 days.

(21) Appl. No.: 12/336,252

(22) Filed: Dec. 16, 2008

(65) Prior Publication Data

US 2009/0168017 A1 Jul. 2, 2009

Related U.S. Application Data

(60) Provisional application No. 61/016,636, filed on Dec. 26, 2007.

(51) Int. Cl.
*A61B 3/107* (2006.01)
(52) U.S. Cl. .................................................. 351/205
(58) Field of Classification Search .......... 351/200–245
See application file for complete search history.

(56) References Cited

U.S. PATENT DOCUMENTS

| | | | |
|---|---|---|---|
| 4,850,691 A * | 7/1989 | Gardner et al. .............. 351/221 |
| 5,317,389 A | 5/1994 | Hochberg et al. | |
| 5,493,109 A | 2/1996 | Wei et al. | |
| 6,004,314 A | 12/1999 | Wei et al. | |
| 6,282,011 B1 | 8/2001 | Tearney et al. | |
| 6,293,674 B1 * | 9/2001 | Huang et al. ................ 351/221 |
| 6,377,349 B1 | 4/2002 | Fercher | |
| 6,549,801 B1 | 4/2003 | Chen et al. | |
| 6,626,535 B2 * | 9/2003 | Altmann ..................... 351/177 |
| 6,704,106 B2 * | 3/2004 | Anderson et al. ........... 356/367 |
| 6,735,463 B2 | 5/2004 | Izatt et al. | |
| 6,741,359 B2 | 5/2004 | Wei et al. | |
| 6,788,421 B2 | 9/2004 | Fercher et al. | |
| 7,246,905 B2 | 7/2007 | Benedikt et al. | |
| 7,330,270 B2 | 2/2008 | O'Hara et al. | |
| 7,364,296 B2 * | 4/2008 | Miller et al. ................ 351/206 |
| 7,374,287 B2 * | 5/2008 | Van de Velde ............. 351/221 |
| 7,400,410 B2 | 7/2008 | Baker et al. | |

(Continued)

FOREIGN PATENT DOCUMENTS

WO WO-0028884 5/2000

(Continued)

OTHER PUBLICATIONS

Baikoff, G. et al. (Sep. 2004). "Static and Dynamic Analysis of the Anterior Segment with Optical Coherence Tomography," *Journal of Cataract and Refractive Surgery* 30:1843-1850.

(Continued)

*Primary Examiner*—Scott J Sugarman
*Assistant Examiner*—Tuyen Q Tra
(74) *Attorney, Agent, or Firm*—Morrison & Foerster LLP

(57) ABSTRACT

An optical coherence tomography apparatus and method for measuring refractive power of the human cornea is disclosed. The apparatus collects both the specularly reflected light from the anterior surface of the cornea and diffusely reflected light from the interior of the cornea. The combined refractive power of both surfaces of the cornea is determined.

28 Claims, 9 Drawing Sheets

U.S. PATENT DOCUMENTS

| | | | |
|---|---|---|---|
| 7,433,046 | B2 | 10/2008 | Everett et al. |
| 7,452,077 | B2 | 11/2008 | Meyer et al. |
| 2004/0088050 | A1* | 5/2004 | Norrby et al. .............. 623/6.11 |
| 2005/0140981 | A1 | 6/2005 | Waelti |
| 2005/0203422 | A1 | 9/2005 | Wei |
| 2006/0228011 | A1 | 10/2006 | Everett et al. |
| 2006/0256343 | A1 | 11/2006 | Choma et al. |
| 2008/0246918 | A1* | 10/2008 | Zhou et al. ................. 351/210 |

FOREIGN PATENT DOCUMENTS

| | | |
|---|---|---|
| WO | WO-2004088361 | 10/2004 |
| WO | WO-2007143111 | 12/2007 |

OTHER PUBLICATIONS

Baumann, B. et al. (Oct. 1, 2007). "Full Range Complex Spectral Domain Optical Coherence Tomography Without Additional Phase Shifters," *Optics Express* 15(20):13375-13387.

Holladay, J. T. (Sep. 1998). "Intraocular Lens Power Calculations for the Refractive Surgeon," *Operative Techniques in Cataract and Refractive Surgery* 1(3):105-117.

Huang, D. et al. (1991). "Micron-Resolution Ranging of Cornea Anterior Chamber by Optical Reflectometry," *Lasers and Surgery in Medicine* 11:419-425.

Leitgeb, R. A. et al. (Nov. 17, 2003). "Real-Time Assessment of Retinal Blood Flow with Ultrafast Acquisition by Color Doppler Fourier Domain Optical Coherence Tomography," *Optics Express* 11(23):3116-3121.

Park, B. H. et al. (May 30, 2005). "Real-Time Fiber-Based Multi-Functional Spectral-Domain Optical Coherence Tomography at 1.3 μm," *Optics Express* 13(11):3931-3944.

Podoleanu, A. G. et al. (Feb. 1, 1998). "En-Face Coherence Imaging Using Galvanometer Scanner Modulation," *Optics Letters* 23(3):147-149.

Tang, M. et al. (Nov. 2006). "Measuring Total Corneal Power Before and After Laser In Situ Keratomileusis with High-Speed Optical Coherence Tomography," *Journal of Cataract and Refractive Surgery* 32:1843-1850.

Vakoc, B. J. et al. (Jul. 11, 2005). "Phase-Resolved Optical Frequency Domain Imaging," *Optics Express* 13(14):5483-5493.

Yasuno, Y. et al. (Mar. 10, 2006). "Simultaneous B-M-Mode Scanning Method for Real-Time Full-Range Fourier Domain Optical Coherence Tomography," *Applied Optics* 45(8):1861-1865.

Zhao, Y. et al. (Jan. 15, 2000). "Phase-Resolved Optical Coherence Tomography and Optical Doppler Tomography for Imaging Blood Flow in Human Skin with Fast Scanning Speed and High Velocity Sensitivity," *Optics Letters* 25(2):114-116.

J.A. Izatt et al., "Micrometer-Scale Resolution Imaging of the Anterior Eye in Vivo With Optical Coherence Tomography," *Arch Ophthalmol*, Dec. 1994, vol. 12, pp. 1584-1588.

* cited by examiner

REFRACTIVE PRESCRIPTION USING OPTICAL COHERENCE TOMOGRAPHY

PRIORITY

This application claims priority to U.S. Provisional Application Ser. No. 61/016,636 filed Dec. 26, 2007, the disclosure of which is incorporated herein by reference.

TECHNICAL FIELD OF THE INVENTION

One or more embodiments of the present invention relate generally to determining the refractive state of the human eye using interferometric tomographic imaging. Determining the refractive power of all or a portion of the refractive surfaces of the human eye is important in prescription of corrective lenses, including the lenses used to replace the natural lens in case of cataract. Devices with sufficient accuracy for refractive prescription are useful in other diagnostic applications, such as detection of corneal irregularities as seen in diseases such as keratoconus.

BACKGROUND OF THE INVENTION

Devices have been proposed to combine the traditional refractive diagnostic instruments with optical coherence tomography and low-coherence interferometry devices. Examples are U.S. Pat. No. 6,799,891 by Barth and U.S. Publication No. 2005/0140981 by Waelti and U.S. Publication No. 2005/0203422 by Wei. Typically, the anterior (front) corneal shape is measured by imaging light reflected from the cornea, and the locations of deeper surfaces, back to the retina, are measured by low-coherence interferometry or some type of tomographic imaging.

Tomographic imaging techniques, such as Scheimpflug imaging, slit-lamp imaging, and optical coherence tomography (OCT), give a cross-sectional image of the refractive surfaces. These methods suffice for measuring the depth of the lens and thickness of the cornea to the required accuracy. Tomographic images alone, however, have not been proven accurate enough to determine refractive power of these surfaces; see for example, Tang et al (2006) who have recently compared the OCT-only approach, with combining OCT with anterior shape measurements from a separate device. The conversion from the measured profile, the "lens sag", of the anterior surface of the cornea to refractive power is 1.3 µm/Diopter, if the sag is measured over a circular patch of cornea with 1 mm radius. Therefore measuring the refractive power to 0.25-Diopter accuracy requires sub-micron resolution of the corneal shape. The diffraction limit makes this resolution very difficult to achieve with non-contact visible light imaging.

Interferometric ranging was shown to locate the corneal surface within 2 µm (Huang et al. 1991) by finding the peak intensity from a specular reflection from the cornea; this publication proposed extending the technique to transverse scanning. A method of using interferometry to determine the shape of the anterior surface of the eye has been described by Hochberg and Baroth in U.S. Pat. No. 5,317,389. Hochberg and Baroth record the interferogram across a line on the cornea in one single snapshot, using bulk optics and an array detector instead of a scanner.

We see the need to determine the complete refractive diagnosis using a single non-contact measurement device. We describe here how to use a single optical coherence tomography (OCT) scanner alone to collect the required information with sufficient accuracy.

DETAILED DESCRIPTION

Figure 1A:
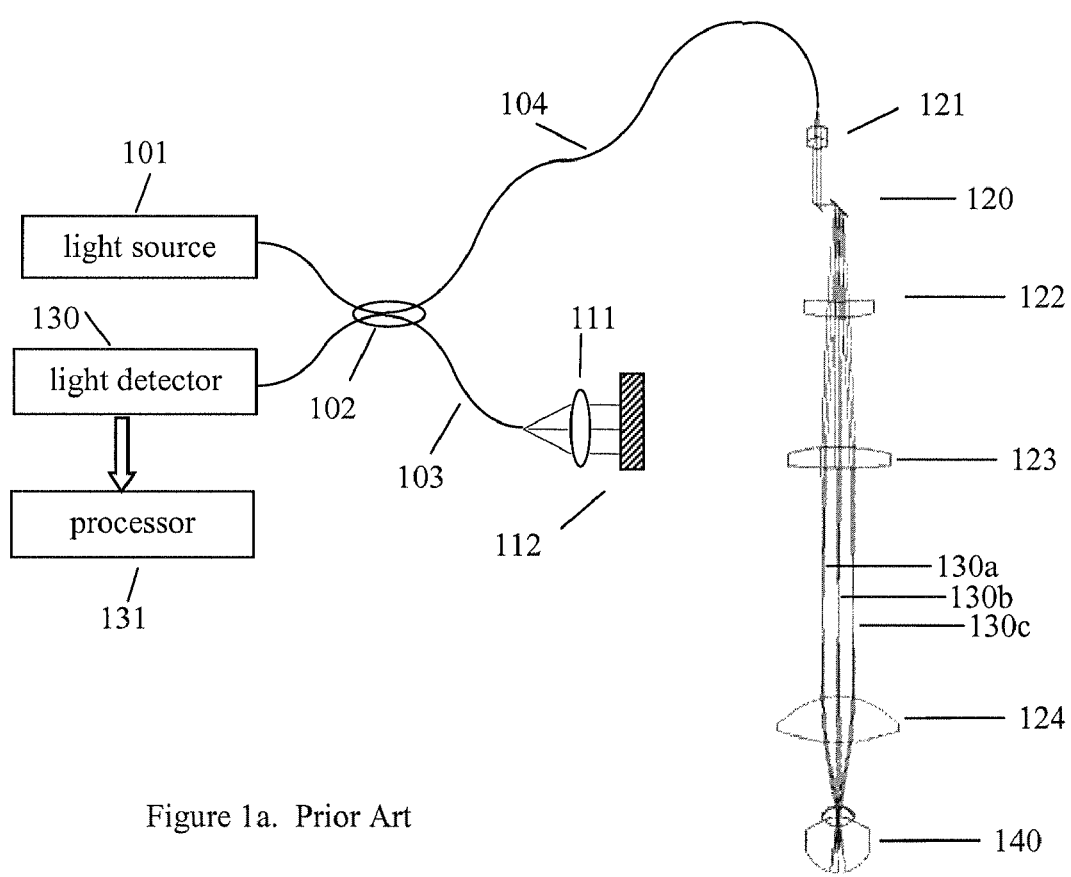
FIG. 1 is a schematic illustration of the preferred geometry for scanning the OCT beam.

We describe an optical coherence tomography (OCT) system configured to scan the eye so that the specular reflection of the scanned beam from the anterior corneal surface is collected as part of the OCT image. The specular reflection locates the profile of the anterior corneal surface, either through the centroid of the specular reflection, or through its phase in phase-sensitive OCT. A set of such profile measurements provides the surface topography of the anterior corneal surface to the degree of accuracy required for refractive prescription. The subject approach provides a more precise measurement compared to the axial resolution available with a conventional OCT system.

In one embodiment, the z-axis (depth axis) location at which the specular reflection has its peak intensity is determined as a function of transverse location. This z-axis location corresponds to the anterior surface of the cornea. It should be noted that typical prior art OCT systems measure diffusively reflected light, except for the occasional specular reflection captured unintentionally, producing an image that is composed of interference speckle. The device herein includes a modification to the OCT scan geometry that permits both diffuse reflections, and specular reflection from a substantial area of the anterior cornea, to be collected simultaneously. In this way, both a conventional OCT image and topographic information are measured the same acquisition.

In another embodiment, the phase of the specularly reflected beam is measured, again as a function of transverse location across the cornea. The phase of this anterior corneal reflection carries sub-wavelength-scale topographic information of the anterior surface of the cornea.

During the OCT scan, axial motion of the patient causes significant errors in the measured topography. Axial motion can be corrected by repeatedly scanning a certain transverse position and inferring motion from the change in axial position of the cornea at that position on successive scans. Alternatively, this motion effect can be corrected by Doppler analysis of the OCT signal from the corneal stroma (the tissue of the interior of the cornea between its surfaces).

The posterior surface of the cornea could be mapped similarly using its specular reflection (either phase or intensity). However, the change in refractive index across the back surface is relatively small, being the difference between refractive index of stroma and that of aqueous humor, both near the index of water. Thus, for our goal of measuring refraction to within a fraction of a diopter, the requirements for measuring the posterior surface elevation are much looser. The resolution of modern OCT systems is sufficient that a tomogram of the cornea locates the posterior surface with sufficient precision for purposes of calculating true corneal power, so isolating a specular reflection from the posterior cornea is not required. This tomogram of the cornea can be created with the same system, and can easily be acquired simultaneously with the specular reflection from the anterior surface.

For prescription of intra-ocular lenses (IOLs) to replace the natural lens in case of a cataract, the distance from cornea to retina is required for prescription, and the positions of each surface of the natural lens are desired for accurate prescription. These distances are conveniently and accurately measured by interferometric means related to OCT (using for example the products IOL Master and Visante from Carl Zeiss Meditec).

In principle the OCT scanner could be configured to scan the entire length of the eye, thereby measuring eye length. However, it is inconvenient to directly image the entire length of the eye with the 2-20 µm resolution desired for the corneal image. In the text below we describe double-exposure methods to measure the required 8-40 mm distances using an imaging range of 2-8 mm only.

Scanning Geometry

The front corneal surface produces the specular reflection traditionally used by reflective corneal topographers (such as the commercial product Atlas) and keratometers (such as the one included in the commercial product IOL Master). The same reflection appears in an OCT tomogram, if the optics is designed to capture the specular reflection. The amplitude and phase of the specularly reflected light vary smoothly across the reflection, in contrast with the rough appearance of speckle from diffusely scattering tissue. The amplitude of this reflection falls off as the corneal surface becomes mis-aligned to the scanning OCT beam, so an inverted arc scan geometry (shown in FIG. 1b-c) is used to keep the beam at near-normal incidence to the cornea over a large region.

FIG. 1a is a schematic illustration of a typical OCT system for imaging the interior of the human eye. The light source 101 provides light to the fiber-based interferometer. Directional coupler 102 serves to split the light from source 101 between a reference arm 103 and a sample arm 104. Lens 111 and mirror 112 serve to return reference light back to coupler 102. A scanning system including scanning mirrors 120, and lenses 121, 122, 123, and 124, directs the light beam successively along paths such as 130a, 130b, 130c onto successive locations within sample 140. Some light scattered from sample 140 returns closely enough along the illumination path to re-enter the fiber interferometer, and is combined with reference light in coupler 102. The interfered sample and reference light are detected in detector 130 after passing through a fiber (detection arm) extending between the coupler 102 and light detector 130. Processor 131 converts the detected interference signals to a cross-sectional image, the tomogram.

Figure 1B:
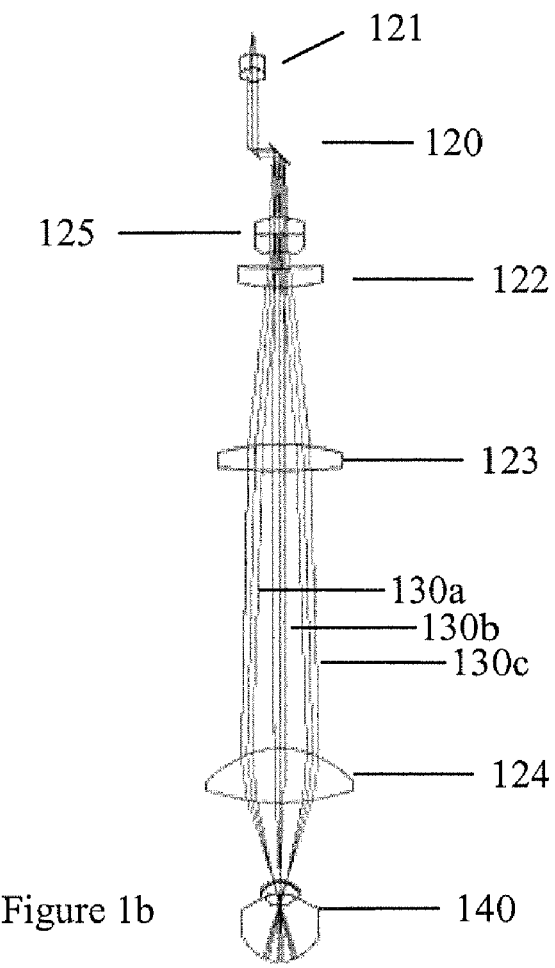

FIG. 1b illustrates one way to arrange the optics in order to apply the presently disclosed method. The fiber portions can remain the same as in FIG. 1a so they are not shown. The configuration of FIG. 1b scans the OCT beam in an arc across the cornea, maintaining always near-normal incidence to the anterior corneal surface. The configuration also brings light beam 130 to a focus near the cornea. (The focus of beam 130 preferably follows the curve of the cornea as the beam is scanned, as described in U.S. Pat. No. 6,741,359). The numerical aperture at this focus is large enough to allow some tolerance of the beam about perpendicular incidence to the cornea, and still collect sufficient specularly reflected light back into the sample path 104. The high sensitivity and wide dynamic range of OCT as a technology is a great benefit here, because the collected portion of the anterior corneal reflection can vary by more than a factor of 1000 as the beam is scanned, and still be properly detected and reconstructed into the tomogram. The specular reflection is preferably collected over at least the central 3 mm of the cornea. The typical diameter of the pupil in a human eye is 3 mm, and we want accurate measurements of at least the transverse extent of the cornea that refracts light that will go into the pupil and be used for vision.

The specific change between FIGS. 1a and 1b is the addition of lens 125, which is one way of producing the desired scan geometry. Lenses 122-124 of FIG. 1a served to relay the collimated scanning beam emerging from scanner 121 onto the pupil of the human eye 140, so that the pivot points of the scanner are relayed near the pupil of the eye. In FIG. 1b, lenses 122-124 continue to serve this relay function, but the added diverging lens 125 makes two changes. First, the OCT beam is now diverging instead of collimated, as if it had come from beam focus just upstream of scanner 120. The relay system transfers this virtual beam focus to a real beam focus, located a corresponding distance upstream of the pupil of eye 140. The power of lens 125 is chosen so that this real focus is near the cornea of eye 140. Second, the effective pivot points of scanner 120 are moved downstream, because the diverging lens 125 makes a virtual image of scanner 120 that is closer to the lens 125 than the physical scanner location. The lens elements 122-124 relay the pivot points to a location deeper in the eye 140 than the pupil, and the location of lens 125 is chosen so that the relayed pivot points of the beam are approximately at the center of curvature of the cornea (this center of curvature being typically 4 mm deeper than the pupil).

Figure 1C:
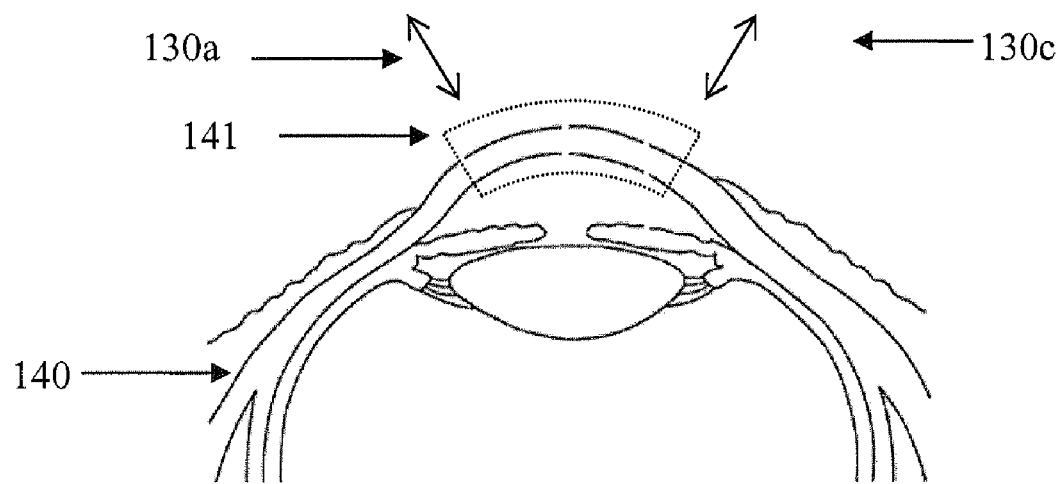

FIG. 1c shows schematically a closer view of the scan geometry across the cornea. The region 141 indicates the extent and shape of the image. The images (tomograms) shown later will be presented in the conventional rectangular shape, with the depth along the beam shown as always the vertical axis, but we keep in mind that the actual scanned region is the arc segment 141.

Locating Corneal Surfaces from the Intensity Image

Figure 2:
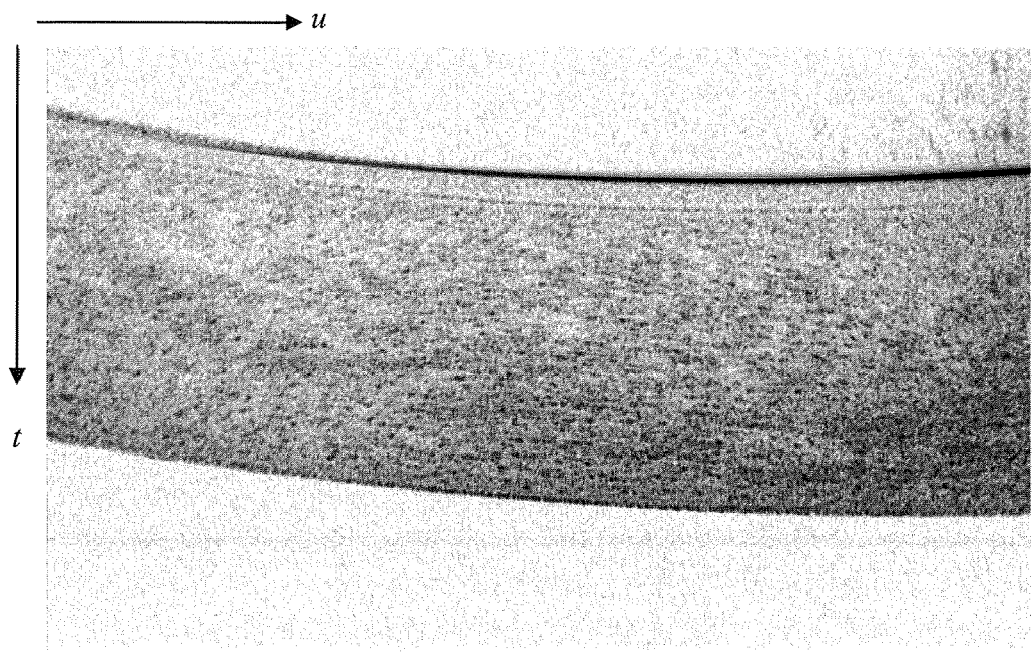
FIG. 2 shows an OCT image of a cornea.

FIG. 2 shows a corneal tomogram in which darker shades of grey indicate greater detected interference signal. Each column of the tomogram corresponds to one of the paths of the OCT beam such as those illustrated before as 130a-c. The vertical location of any feature in the image corresponds to the optical delay along the beam path 130 to the corresponding feature in the sample. Specifically, signal processing theory well known in the field of OCT tells us that the relevant delay is the group delay, as distinct from the phase delay. The group delay is conceptually the time required for an optical pulse travel any particular distance along the beam path 130. Thus the separation between the top and bottom corneal surfaces as they appear in FIG. 2 is the distance the beam traveled through the corneal tissue, times the group index of corneal tissue.

Most of the image in FIG. 2 is composed of speckle, but the anterior surface of the cornea (the upper surface in FIG. 2) appears as one continuous high-reflectance region, curving from the right side to nearly the left side of FIG. 2. The continuous nature of this reflection allows us to find the curve that follows its center, from left to right across the image. The curve along the center of the continuous reflection can be located with a precision much better than the axial (vertical) extent of this reflection, which axial extent is the axial resolution of the OCT system. We want to extend the function of processor 131 to find the anterior surface automatically. One way to automatically locate this curve in the image is to find the lowest-cost path from left to right across the image, where the cost function is the negative of the intensity of the reflectance signal.

The posterior surface of the cornea (the lower surface in FIG. 2a) can be found by segmenting the tomogram using the usual methods of OCT image processing. Whereas the continuous reflection across the anterior surface allows the lowest-cost-path to be found on the image directly, finding the posterior surface requires substantial smoothing of the image until the speckle contrast is reduced to below the level of contrast between corneal stroma and aqueous humour. Then the vertical gradient of the intensity in the smoothed image will have a maximum at the boundary that exceeds the local maxima and minima due to speckles. After smoothing, the vertical gradient of the smoothed intensity will have a minimum at the posterior boundary. This gradient can then serve as the cost function for a lowest-cost path algorithm to find a path that approximately follows the posterior corneal surface. The precision of locating the posterior surface from an image such as FIG. 2 is limited by the size of the speckle, the axial dimension of speckle being the axial resolution of the OCT device. This precision is sufficient for refractive prescription, because the change in refractive index across the surface is much smaller than at the anterior surface. The smaller change in index means that the refraction at the posterior surface is much weaker than that at the anterior surface, so any error in finding the surface has relatively less effect on predicted total refractive power of the cornea.

Knowing the scan geometry, one can perform the coordinate transformation from the coordinates of FIG. 2 to real space. The coordinates of FIG. 2 are the progress of scanner 120, denoted by u, and the optical group delay to each surface, denoted by t. The curves in real space are plotted in FIG. 3, with the anterior corneal surface plotted above, and the posterior corneal surface plotted below. Refraction of the OCT beam at the anterior surface has a small effect on the transformation from scan coordinates (t, u) to real space coordinates of the posterior surface.

Using the Phase Information in the Tomogram

Figure 4A:
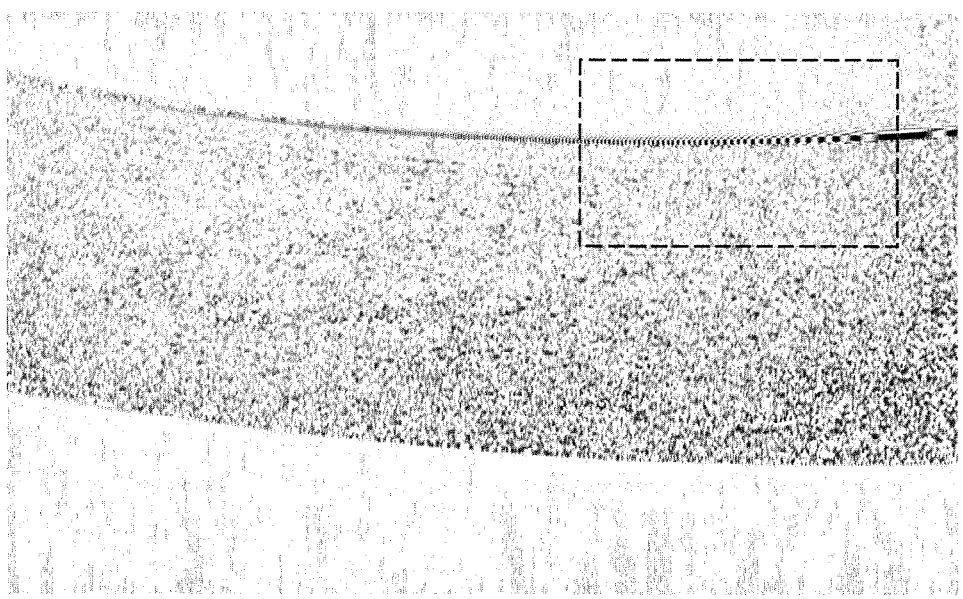
FIGS. 4A and 4B show the OCT images of a cornea, with modulation based on the phase of the reflections from the cornea.
Figure 4B:
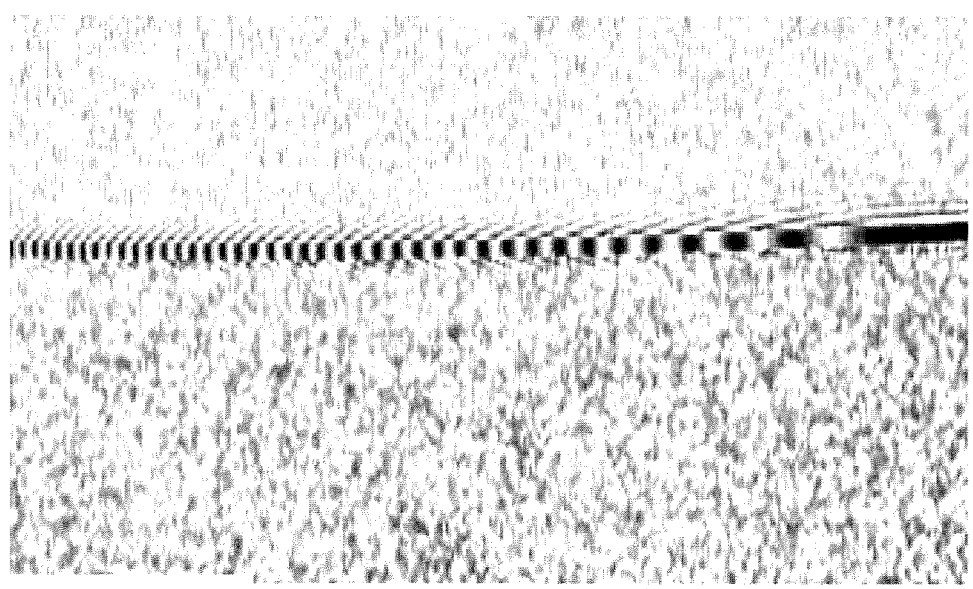
Figure 5A:
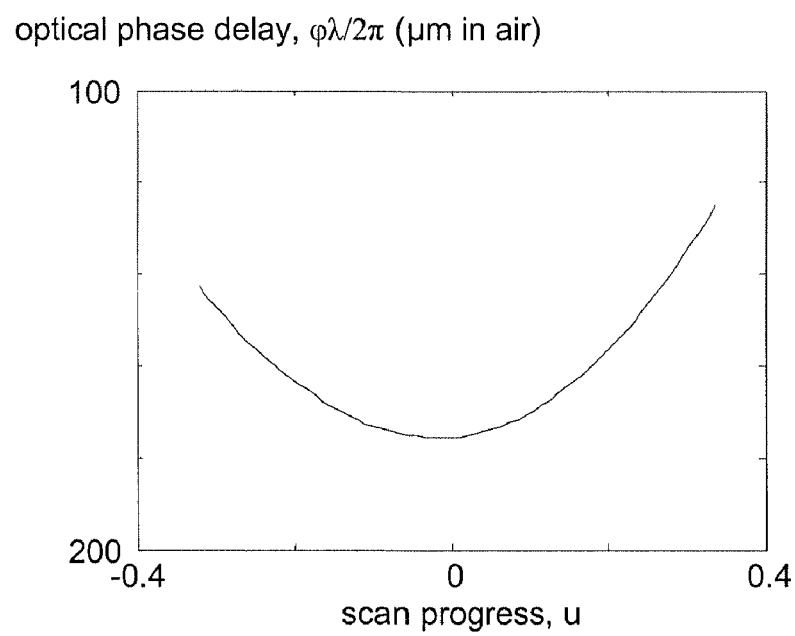
FIG. 5 plots the optical delays to the anterior surface of a cornea, determined by two methods described herein.

Optical Coherence Tomography is an interferometric technique, so it can provide the phase of the interference signal at each point on the tomogram. FIG. 4 shows the same image as FIG. 2, but FIG. 4 is modulated according to the phase $\phi$ of the detected interference signal. (Specifically, FIG. 2 shows log $(I+I_0)$ where I is the intensity of the interference, and $I_0$ is a reference intensity, and FIG. 4 shows log$(I+I_0)$ multiplied every point by 1+cos$\phi$.) FIG. 4a shows the same extent of the cornea as did FIG. 2, while FIG. 4b shows a smaller region, indicated by the dashed box in FIG. 4a, magnified to make the fringe structure visible. One sees that the continuous reflection at the anterior corneal surface has continuously changing phase, indicated by the smoothly-oscillating intensity across the top surface in FIG. 4. Each cycle in phase $\phi$ corresponds to a difference of one-half wavelength (of the light used in the OCT beam) in z of the corneal surface, relative to the surface of constant phase of the scan beam. The curve in FIG. 5a shows the integrated phase of this reflection, multiplied by $\lambda/2\pi$ where $\lambda$ is the central wavelength of the OCT beam at which the phase is measured. Thus FIG. 5a plots the phase delay to the anterior corneal surface, as a function of scan progress u.

The posterior surface of the cornea could be measured in a similar manner by recording its specular reflection. The phase difference between anterior and posterior reflections is equal to the local thickness of the cornea times its phase index. This product is exactly what is required in an optical model. It is sufficiently accurate, and generally more convenient, to locate the posterior corneal surface from the intensity image as described above.

Figure 3:
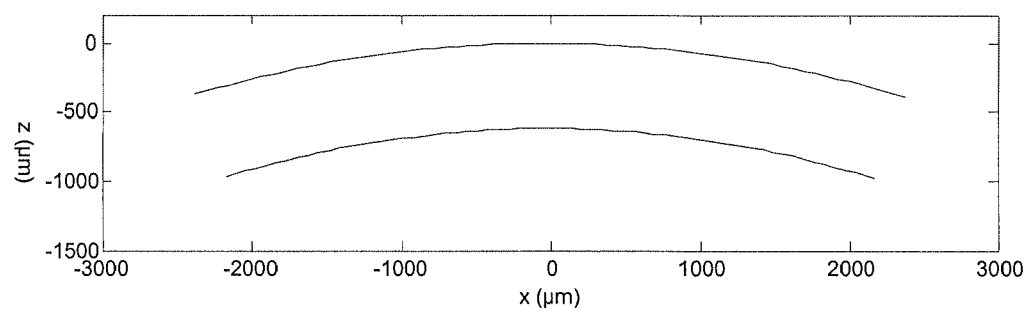
FIG. 3 plots the profiles of the anterior and posterior surfaces of a cornea.
Figure 5B:
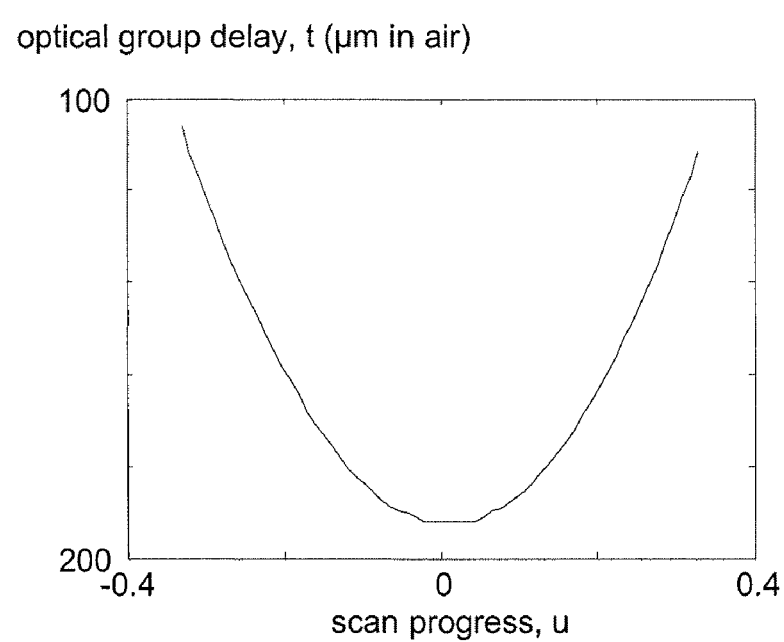

From the curve in FIG. 5a in scan coordinates, a similar coordinate transformation to real-space coordinates x and z gives an alternative determination of the anterior corneal profile, comparable to the information in the upper curve of FIG. 3 but this time with even better sub-wavelength precision in locating the anterior corneal surface. For comparison with the phase delay profile in FIG. 5a, the curve in FIG. 5b shows group delay profile, determined from the apparent height of the specular reflection in the OCT tomogram FIG. 2a. Some important between these measures of the anterior corneal profile are explained next.

Details of Determining Coordinates from the OCT Images

Some optical details regarding the OCT instrument become noticeable on the scale of the micron-scale heights we are measuring.

First, the phase delay along OCT beam 130 is different from the group delay along the OCT beam. When the OCT beam is scanned through the center of the lenses in the optical system, it passes through more glass. One can calculate the delays by determining the physical path length of the beam through each type of glass, using ray tracing software, and then forming the weighted sum of the path lengths, using refractive index as the weight to calculate the phase delay, and group index of the various glasses to calculate the group delay. Passage of the beam through glass typically adds more to the group delay than it adds to the phase delay. For the particular system illustrated in FIG. 1b, we calculate the extra group delay at the center of the optics, relative to that at the edges of the scan, to be equivalent to 60 μm passage through air. One can add this extra group delay to the profile in FIG. 5a in order to bring it into the (t,u) coordinates of the OCT intensity image FIG. 2a and the profile in FIG. 5b.

Second, specular reflections can appear in the reconstructed OCT image at depths different from that of the material causing the reflection. This can be seen at the left side of FIG. 2a and FIG. 4, where the continuous high-reflectance region from the specular reflection appears inside the corneal tissue. The cause of this apparent displacement is lateral color in the imaging system. The red portion of the spectrum used for OCT was scanned transversely slightly more than the blue portion, due to chromatic dispersion of the lenses. At the left side of the tomograms, the red portion of the spectrum sampled the surface further to the left than the blue portion. This separation, coupled with the slope of the reflecting surface, gives a phase delay in the specularly reflected light that depends on wavelength. A wavelength-dependent phase delay causes a group delay. (This effect is used in the field of OCT to create a rapid-scanning optical delay, as described in U.S. Pat. No. 6,282,011.) On return to the scanner, the red end of the spectrum collected from the specular reflection at the left side of FIG. 2 will have less phase delay than the blue end of the spectrum. The greater optical path on the blue end of the spectrum is equivalent to an extra group delay, so the specular reflection is displaced downward in the reconstructed image FIG. 2, indicating a greater apparent distance to the reflection. The specular reflection appears to be slightly inside the scattering tissue, whereas the actual location of reflection is from the top-most surface of the cornea.

In principle the effect discussed in the previous paragraph can be corrected by correcting the transverse magnification of the OCT data set independently for each wavelength, according to the transverse scan of the OCT beam at each wavelength. More practically, the curve as in FIG. 5a that traces this reflection can be corrected, once the magnitude of the effect is determined for the particular scan optics. In the example given here, the extra apparent depth due to lateral color varies from zero along the optical axis to 290 μm times the slope of the reflection at the ends of the scan.

One also needs to be aware that the anterior surface reflection does not always appear to be all the way at the anterior of the cornea, in the OCT tomogram, when choosing the algorithm to isolate the front-surface reflection from the image.

Third, the anterior corneal surface may reflect the OCT beam at a point not exactly in the beam focus. If the anterior surface is a distance d further along the OCT beam than the focus of the OCT beam, and if the surface has slope s relative to being perpendicular to the beam, then the surface will selectively reflect back into the sample arm 104 those OCT rays with a slant s relative to the chief ray. From the geometry of the triangle formed by the chief ray, the anterior surface, and the rays that are reflected to the sample arm, one can see that the detected rays hit the surface a distance approximately $d \times (1-s^2/2)$ beyond the focus, whereas the surface is a distance d beyond the focal point as measured along the chief ray. The surface appears too high by $ds^2/2$. This effect is typically a few microns or less, but again can be corrected based on the curve of the anterior reflection, once the position of the beam waist is measured in relation to the extent 141 of the captured tomogram.

Patient Motion Along the Instrument Axis

Patient motion will affect the measured shape of the surface, because the axial scans (A-scans, the columns in the image of FIG. 2) are not collected simultaneously. Axial motion, along z, of the patient's eye, when the head is placed in a typical ophthalmic chinrest, can be as fast as 2 mm/sec, with oscillation frequency up to 8 Hz. The corresponding axial acceleration is 0.1 m/s², which will be used below. In addition, we observe brief axial accelerations greater than 6 m/s².

This axial motion has a significant effect on the estimated corneal power. By comparing the change in height z as a function of time t due to axial motion of the patient with constant axial acceleration a, $$z = at^2/2,$$

to the change in height z as a function of transverse position x due to curvature of a cornea with radius R, $$z = (x^2/R)/2,$$

one can see that the motion-induced error in measuring the curvature 1/R is $$\Delta(1/R) = a/v^2$$

where v is the constant transverse-scan speed of the measurement beam, so that x=vt. If one collects A-scans spaced transversely by 50 μm, at a rate of 2000 Ascan/sec, the transverse scan speed across the cornea is v=0.1 m/s. In this case for a typical patient acceleration of a=0.1 m/s² we have an error $\Delta(1/R)=10/m$. The corresponding error in refractive power of the anterior corneal surface is unacceptably large at $(n-1)\Delta(1/R) \approx 3.8$ Diopters, where we have used n=1.376 as the index of refraction of the cornea.

Figure 6:
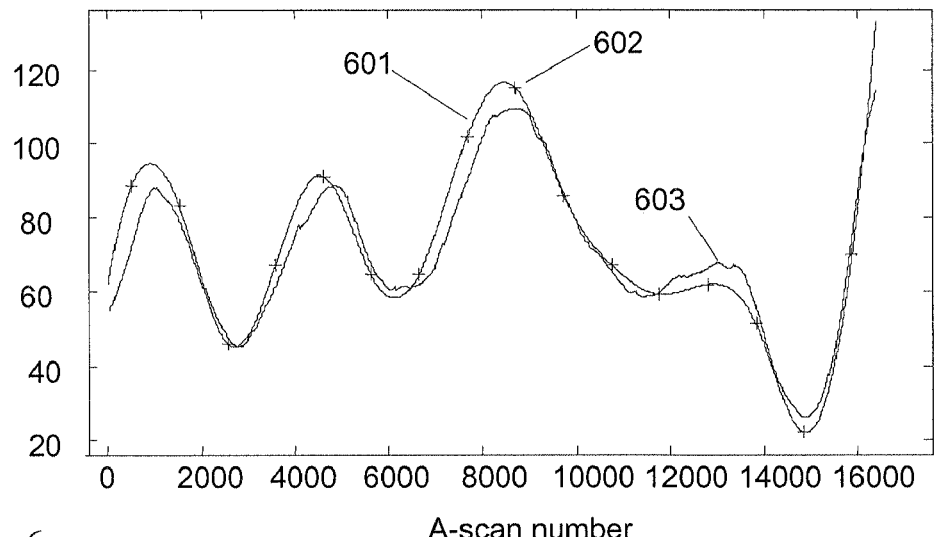
FIG. 6 is a plot of the detected motion of the human eye during acquisition of several tomograms.

The axial motion during the scan can be easily determined by scanning repeatedly across the fixed position. A preferred scan pattern for this application is the star-shaped pattern of scan planes shown in FIG. 1 of U.S. Pat. No. 7,452,077. The OCT scan beam repeatedly scans across the center of the star pattern. At each measurement in the center of the star pattern, if there is patient motion, the measured height of the cornea at that location will be different. FIG. 6 shows these height measurements as the '+' symbols 602. Heights 602 could possibly have been measured at different locations on the cornea, if there was transverse motion as well. However, in this application the central cornea is of most interest, so the patient is typically aligned so that the highest point of the cornea is nearly centered on the instrument axis. In this case the slope of the corneal surface is small where they intersect the instrument axis, so transverse motion has only small effect on the distance to the corneal surface along the instrument axis.

A spline fit 601 through the measured heights, being the interpolating curve with minimum acceleration, is the preferred estimate of the continuous axial patient motion. The motion estimates from the spline fit 601 in FIG. 6 are applied to the z positions in the real-space corneal profiles of FIG. 3.

Axial motion during the OCT scan can also be measured using the Doppler shift information inherent in the OCT signal. The scattering from the stroma, appearing in FIG. 2 as the speckle field below the strong anterior surface reflection, has an associated Doppler shift proportional to the relative motion between the patient and the OCT scanner. Extraction of the axial velocity from this Doppler shift has been described by Izatt et al in U.S. Pat. No. 6,735,463, for example. The Doppler information is inherent in interferometry, and therefore is available in various detection schemes such as time-domain OCT (for example U.S. Pat. No. 6,735,463 and U.S. Pat. No. 6,549,801) spectral-domain OCT (for example Optics Express 11(23): 3116-3121 from Leitgeb) and swept-source OCT (for example Optics Express 13(11): 3931-3944 from Park).

The precision of Doppler information is easily sufficient to correct the anterior surface measurements for purposes of refractive prescription. The variance (square of the standard deviation) of individual phase measurements in Doppler OCT is known to be the inverse of the signal-to-noise-ratio; see for example Park et al. (Optics Express 13(11): 3931-3944). In this application the signal-to-noise ratio is typically 10 for corneal stroma; averaging the signal over the full corneal thickness increases the SNR to about 40. Thus the individual Doppler phases have variance about 0.025 radians², corresponding to standard deviation 0.15 radians, which is only 0.03 μm for the near infrared wavelengths used in OCT of the eye.

A preferred way of computing this depth-averaged Doppler effect uses two successive axial scans, $r_1(z)$ and $r_2(z)$, containing the measured reflection coefficients r as a function of depth z in the scan. The reflection coefficients here are have magnitude proportional to the measured interference fringe amplitude, which is in turn proportional to the reflected electric field, and phase determined by the interference fringe phase. The phase of the product $\text{conj}(r_1) \times r_2$, where conj( ) denotes complex conjugate, is on average the Doppler phase due to bulk motion of the patient, and other Doppler effects considered later. There will be local variations in the phase of $\text{conj}(r_1) \times r_2$ due to noise and due to slightly different tissue being sampled in the two axial scans. The product $\text{conj}(r_1) \times r_2$ is integrated over a range of depths z starting below the specular reflection from the anterior corneal surface, and preferably ending above the specular reflection from the posterior corneal surface if this reflection is collected, while including as much reflection as practicable from the stroma. This method can be applied to axial scans $r_2(z)$ measured using time domain OCT (as in U.S. Pat. No. 6,549,801 by Chen et al) or swept source OCT or spectral domain OCT. The patient motion estimated by such Doppler phases is plotted as curve 603 in FIG. 6.

One might consider making certain corrections to the measured Doppler shift, related to the bending of light at the anterior surface, the shorter wavelength inside tissue, or other refractive effects. Corrections for these effects are not required, however, to measure the change in anterior surface height due to patient motion. This can most easily be seen by considering the entire path length of the OCT beam in the presence of refraction and patient motion; the only section of the path that changes length is the section in air, which is precisely the distance measurement we need to correct.

Another potential complication is that the transverse scan across a potentially-sloping corneal surface changes the path length in air, seemingly producing a Doppler shift independent of patient motion. Again we are spared the complication, this time because the rays of light that reaches a given scatterer, from successive steps in the transverse scan with an ideal scanner, have identical total phase delays. This can be verified by applying Fermat's principle, assuming an ideal scanner, or by experiment.

The Doppler effects due to the scanner itself, such as the effect of misalignment of the beam on scanning mirrors as described by Podoleanu (Optics Letters 23(3): 147-149 (1998)), can be compensated. Such effects cause an additive offset to the measured surface, which is fixed for a given measurement device, so they can be absorbed in system calibration, such as by measuring a surface of known shape.

Transverse Motion

Transverse motion of the patient has the effect of compressing or expanding the transverse scale, x in the expressions above, by some percentage given by the ratio of patient motion to scan speed. This creates an error of the same percentage in measured corneal power. Transverse motion tends to be smaller, approximately 1 mm/sec, so with the same 0.1 m/sec scan speed, transverse motion results in approximately 1% error in power. This error may be tolerable in many applications. If not, straightforward error cancellation methods can be applied, such as alternating the direction of the transverse scan so as to measure twice with equal and nearly opposite errors. U.S. Pat. No. 7,452,077 describes a correction method specifically applicable to the cornea. We describe below an alternative method of estimating and approximately correcting transverse motion, using speckle correlation. Such efforts can reduce the effects of transverse motion to tolerable limits.

Speckle Correlation to Estimate Transverse Motion

Figure 7:
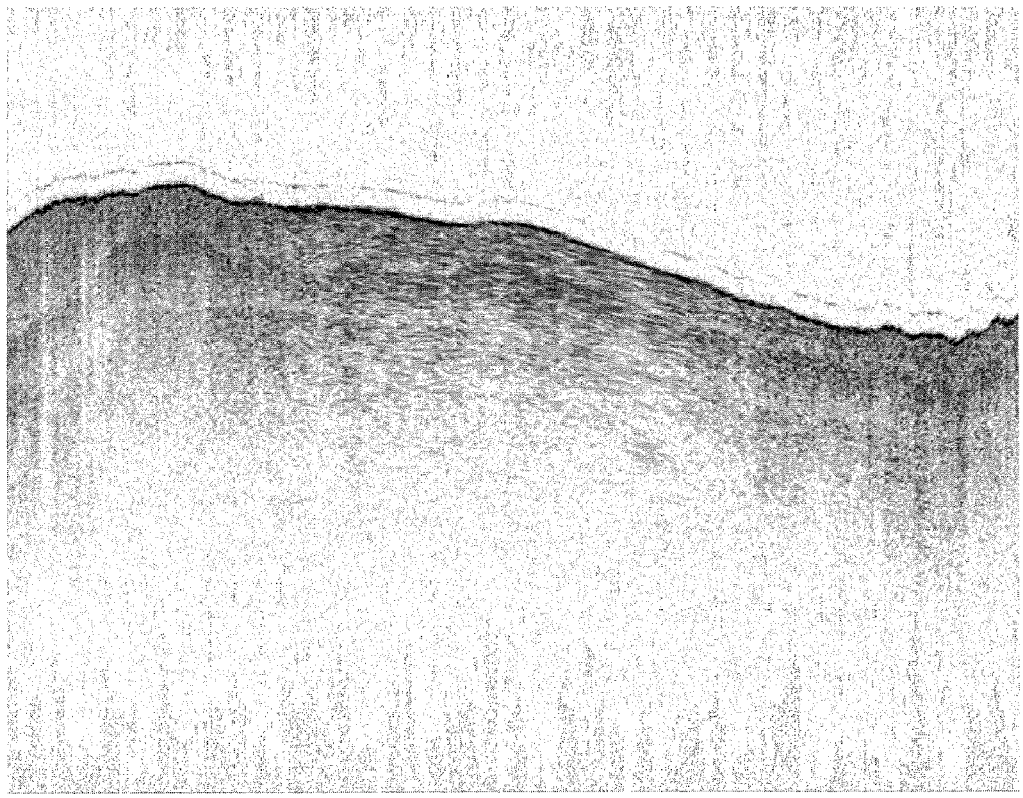
FIG. 7 shows an OCT image of skin tissue, imaged using irregular transverse scan speed.

The speckle in OCT images has a transverse size w, in real space, determined by the transverse resolution of the imaging optics. If one scans transversely across a sample that is moving transversely, the sampling of axial-scans (A-scans) will not be uniform in real space, so the resulting tomogram will have apparent speckle changing size across the image. FIG. 7 shows such a tomogram, measured on the skin of a finger instead of an eye for the sake of practical experimentation with different motions.

Analysis of the changing apparent speckle size allows us to estimate the relative transverse speed between the scanning beam and sample, according to the following principle:

$$\text{relative transverse speed} = k\, w/(n\, t)$$

where w is the transverse size of the speckle determined by the optics, n is the number of A-scans over which speckle are correlated within some local portion of the recorded tomogram, and t is the time between the acquisition of successive A-scans.

Our preferred estimate of correlation between A-scans is the normalized cross-correlation, choosing the maximum value over all realistic offsets in the axial, z, direction (analogous to selecting the delay corresponding to maximum correlation between two signals). Conceptually, the number of correlated A-scans n for a given region of the tomogram is the maximum separation n between a pair of A-scans selected from the acquisition sequence for which the pair has normalized cross correlation above some threshold. For better rejection of noise, the cross-correlation is computed as a function of separation between A-scans; the decay of this cross-correlation function with separation is fit to a typical decay curve freely scaled along the axis denoting separation, and the best-fit scaling is proportional to the correlation number n. In a real-time implementation, each A-scan is correlated only with previously-acquired A-scans.

Figure 8:
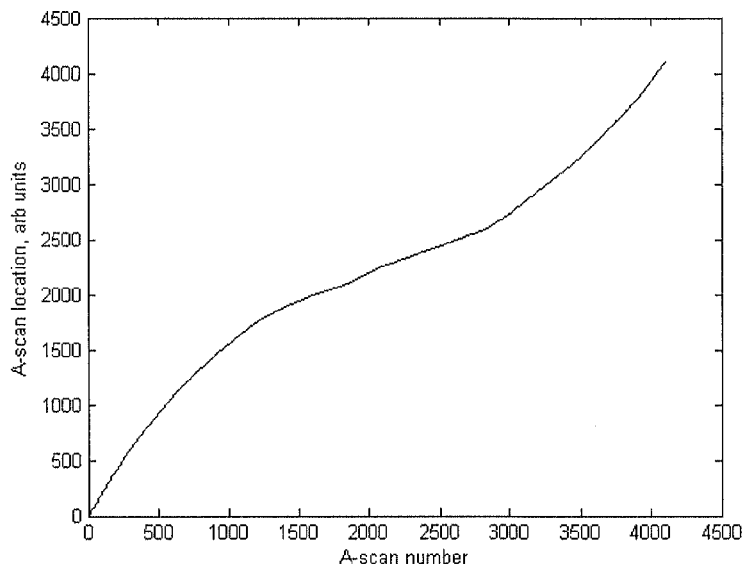
FIG. 8 plots the estimated transverse position, relative to the tissue being imaged, of each column in FIG. 7.
Figure 9:
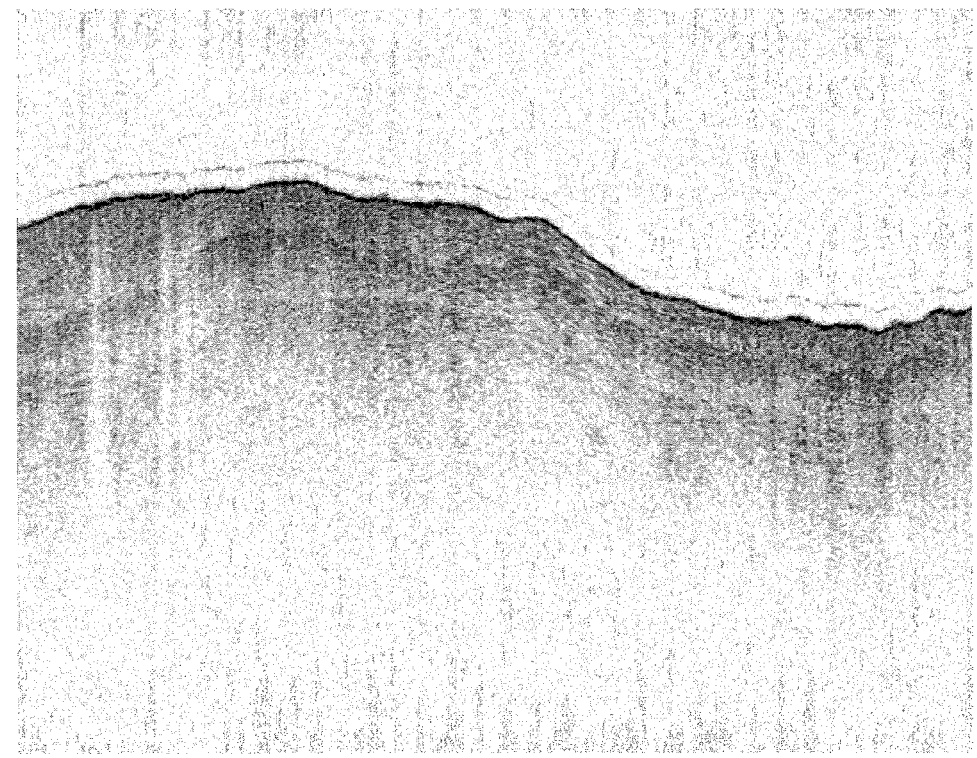
FIG. 9 shows the tomogram of FIG. 7, approximately corrected for transverse motion

After calculating the speed, the transverse position is calculated by integrating the speed. The integrated speed is shown in FIG. 8, which relates A-scan number to a transverse distance along the sample. For a given scanner and class of sample, one can often choose an effective filter for the relative speed based on the plausible motions of the sample. (FIG. 4 in US Application Publication 2006/0228011 shows the results of filtering eye position data in a similar situation.) The A-scans from FIG. 7 are placed according to the curve of FIG. 8 to produce the tomogram in FIG. 9.

Another application of this method for determining transverse speed of a scan is in handheld OCT probes. Disposable OCT probes for retinal surgery have been proposed (for example, Wu, et al., "Paired-angle-rotation scanning optical coherence tomography forward-imaging probe." Optics Letters 31(9): 1265 (2006)) which could be used for scanning the retina during surgery. The proposed probes have counter-rotating prisms to create a linear scan pattern. However, the cost and complexity of these probes may be too high for practical use. Alternatively, during retinal surgery surgeons already have handheld, disposable probes for delivery of laser beams to the retina. A similar non-scanning probe may be used to create an OCT image if the surgeon manually scans the probe across the area of interest. The resulting image will have a scan speed which is not known a priori but which can be deduced by measuring the size of speckle cells in the resulting image. The displayed image is scaled in the x-direction accordingly.

Refractive Power of the Cornea

The refractive power of the cornea can be determined from the corrected profiles of the anterior and posterior surfaces. A set of tomograms including FIG. 2a were created by scanning a beam across the cornea in a star pattern at various angles as seen from the front of the patient. The tomogram collected from each of these scan planes contains a continuous specular reflection from the anterior corneal surface that gives an accurate profile of the anterior cornea, and the usual OCT image, derived from the diffusely reflected light, is used to find the profile of the posterior cornea based on standard image segmentation techniques. Thus each tomogram yields a front and back corneal profile as in FIG. 3. The radii of these profiles are found as the radius of best-fit spheres, where the fit preferably weighs the central cornea more heavily. The separation between the profiles gives the thickness of the cornea. From these radii, the central thickness of the cornea, and the refractive indices of the cornea (1.376) and aqueous (1.336), on can derive the refractive power in each scan plane through the thick lens formula. These radii and refractive powers are listed in the table below.

| Scan Plane Angle (degrees) | Anterior Radius (mm) | Anterior Power (diopters) | Posterior Radius (mm) | Posterior Power (diopters) | Total Power (diopters) |
|---|---|---|---|---|---|
| 0.00 | 7.41 | 50.74 | 6.67 | −6.00 | 44.89 |
| 11.25 | 7.31 | 51.44 | 6.42 | −6.23 | 45.34 |
| 22.50 | 7.36 | 51.09 | 6.39 | −6.26 | 45.01 |
| 33.75 | 7.30 | 51.51 | 6.51 | −6.14 | 45.49 |
| 45.00 | 7.28 | 51.65 | 6.60 | −6.06 | 45.71 |
| 56.25 | 7.24 | 51.93 | 6.32 | −6.33 | 45.78 |
| 67.50 | 7.20 | 52.22 | 6.54 | −6.12 | 46.25 |
| 78.75 | 7.17 | 52.44 | 6.12 | −6.54 | 46.04 |
| 90.00 | 7.16 | 52.51 | 6.17 | −6.48 | 46.21 |
| 101.25 | 7.20 | 52.22 | 6.28 | −6.37 | 46.03 |
| 112.50 | 7.13 | 52.73 | 5.84 | −6.85 | 46.04 |
| 123.75 | 7.22 | 52.08 | 6.33 | −6.32 | 45.91 |
| 135.00 | 7.26 | 51.79 | 6.09 | −6.57 | 45.41 |
| 146.25 | 7.31 | 51.44 | 6.59 | −6.07 | 45.50 |
| 157.50 | 7.33 | 51.30 | 6.48 | −6.17 | 45.24 |

This eye has central corneal thickness of 630 µm, and shows 45.6 diopters spherical-equivalent power, plus 0.7 diopters of cylinder. The measurements of posterior radius fluctuate more strongly due to uncertainly in finding the surface through speckle. Inclusion of higher-order aberrations to describe the surfaces in more detail can be done as known in the art.

Calibration

Accurate knowledge of the scan coordinates is important in this application. If the optical delay along the sample path were to drift by 50 µm, by thermal drift in the optical delay through a fiber for example, then the image data would be placed incorrectly in the arc-scan geometry 141 shown in FIG. 1c. The resulting error of 50 µm in the radius of corneal curvature would lead to a 0.3-diopter error in corneal power. The location of the region 141 captured in the tomogram must be known precisely relative to the points about which the OCT beam pivots in each transverse scan direction. These pivot points are the centers of the arc coordinate system.

One way of re-calibrating the instrument in the field is to image a surface of the final lens 124 using the OCT beam. The OCT beam is not in focus at lens 124, but at beam position 130b there will be some small reflection from these lens surfaces back to the sample path 104, and the great sensitivity of OCT makes this reflection easily detectable. The length of the reference path can be set by moving mirror 112 until the reflections from lens 124 are within the scan range of the OCT system. The optical delay to the surfaces of lens 124 has quite consistent offset from the optical delay to the pivot points of the OCT beams.

Similarly, the transverse coordinate u of the OCT scan can be re-calibrated by using the OCT scanner to locate the edges of lens 124.

Lens Location

Anterior chamber depth (ACD) and lens thickness (LT) of the natural human crystalline lens are used in the prescription of intraocular lenses to estimate the location at which the intraocular lens will lie. These distances have been measured using optical coherence tomography (for example Journal of Cataract & Refractive Surgery 30(9): 1843-1850 (2004) by Dr. Baikoff). Not all OCT devices, however, have the depth range required to image the entire anterior chamber and lens. Each of these structures is approximately 4 mm deep, while high-resolution OCT specializing in imaging the retina or cornea needs only 2 mm depth range on any given image. Fourier-domain OCT techniques in particular suffer from a mirror image artifact that makes imaging large depth ranges more difficult.

For the tasks of refractive prescription, however, high-quality imaging is not required; one need only determine the location of the anterior and posterior surfaces of the natural lens, relative to the anterior corneal surface. The shape of the natural lens does not need to be measured for intraocular prescription, as it will be removed before the intraocular lens is inserted; only its location need be measured to predict the location at which the intraocular lens will lie. Approximate corrections for the mirror image are sufficient for this purpose.

Approaches for Dealing with the OCT Mirror Image

Figure 10A:
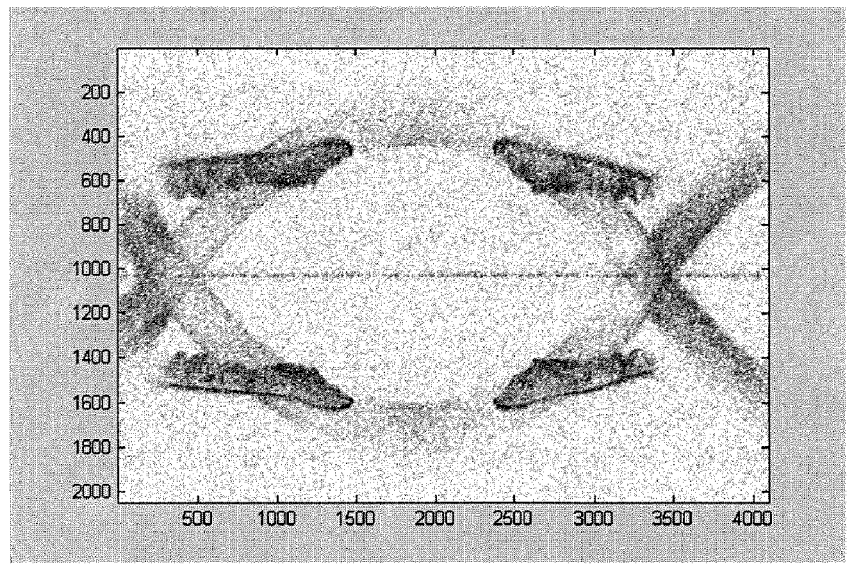
FIG. 10 shows OCT images of the anterior portion of the human eye, including the mirror image artifact characteristic of spectral domain OCT scanners.
Figure 10B:
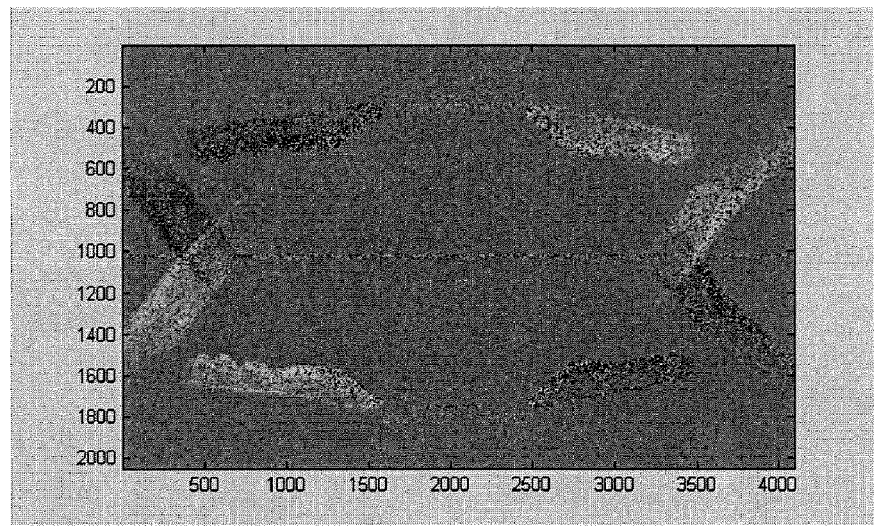

FIG. 10a shows an image of the anterior chamber recorded by a spectral-domain OCT system. The mirror image complicates interpretation of the image. FIG. 10b shows an image derived from the OCT information in FIG. 10a, in which the local Doppler signal of patient motion determines whether the tissue is shown in white or black. The upright image moves in the opposite direction to the inverted image, so the Doppler information disambiguates the double image. The left portion of the Doppler image FIG. 10b shows the upright image of the cornea in white, and the inverted image in black. During the FIG. 10 scan, patient motion reversed. The right portion of FIG. 10b has the upright image of the cornea in black, and the inverted image in white. If one captures a few of such Doppler images in sequence, eventually patient motion will make the upright image completely white.

Rather than depend on patient motion, it would be preferable to design the scanner to create a reliable phase shift $\psi$ between successive axial scans A and B. With minor adjustment to the typical OCT scanner, one can add a controlled phase shift $\psi$ known, for example by offsetting the beam on the scanning mirrors (Podoleanu in Optics Letters 23(3): 147-149 (1998)).

In a primarily-retinal OCT scanner, a convenient way to enable such a phase shift simultaneously with selecting focus on the anterior chamber would be to flip a lens into the OCT scan path, before the beam reaches the scanning mirrors. This lens should have the proper power to move the beam waist from retina to anterior chamber, and proper prism to shift the beam from centered on the scanner (no Doppler shift) to offset by an amount comparable to the beam diameter on the scanner.

The controlled phase shift can also be easily added elsewhere in the optical path, for example by using the spinning disk of variable optical delay described in U.S. Pat. No. 7,433, 046. The use of separate devices for scanning and phase shifting provides more flexibility choice of scan patterns.

Fercher describes uses of phase shifting in spectral domain OCT in U.S. Pat. No. 6,377,349. One can cancel errors in setting the phase v by making three measurements at equally-spaced phases, $$C=re^{-i\psi}+r_m e^{i\psi},\ A=r+r_m,\ B=re^{i\psi}+r_m e^{-i\psi},$$

as suggested by Fercher. These measurements are combined in a way that cancels errors in setting the phase $\psi$. The combination A−i(B−C)/(2 sinψ) gives 2r, where r is the desired reflected field that yields the upright image, and if $\psi$ is near 90° then errors in the estimation of $\psi$ have little effect on the result. Such redundant measurements make practical the use inexpensive methods to approximate phases $\psi$, such as the beam misalignment on the scanning mirror, or the spinning disk with smooth thickness variation instead of steps.

Figures 11A, 11B, 11C:
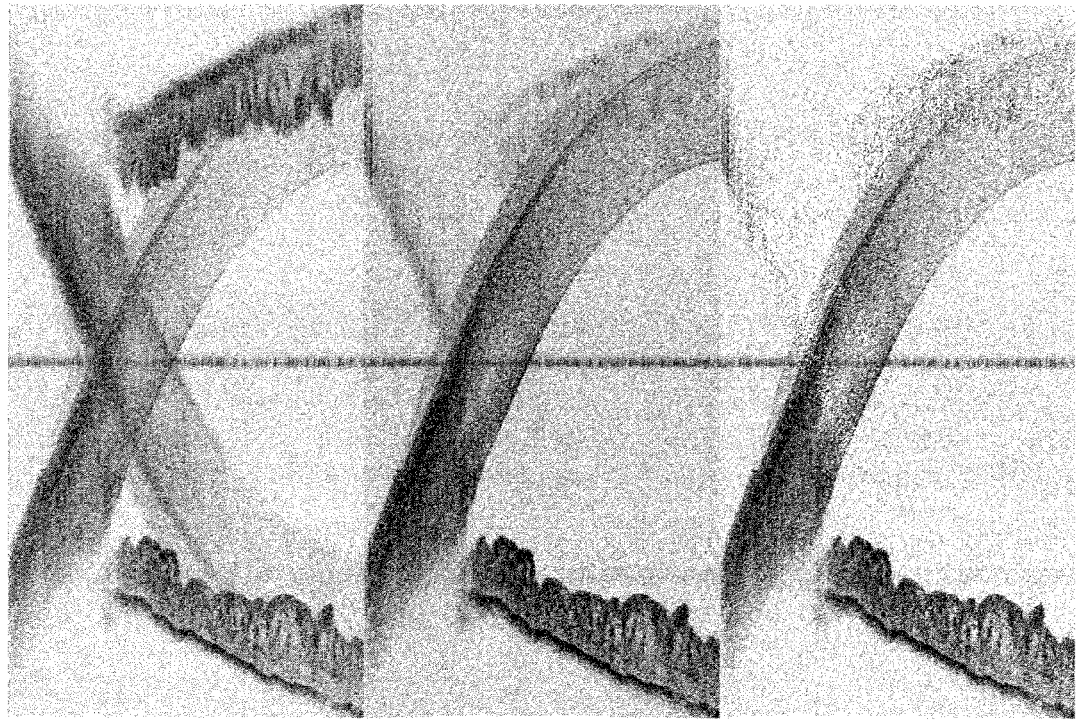
FIG. 11 shows OCT images resulting from the use of phase shifts and Doppler information to suppress the mirror image artifact.

FIG. 11b shows the results of such a three-phase measurement, compared to the reconstruction of a single measurement in FIG. 11a. The phase shifting technique can be extended to a larger number of measurements, in such a way that no prior knowledge of the precise phase shift $\psi$ is required for reconstruction (Yasuno *Applied Optics* 45(8): 1861, Baumann *Optics Express* 15(20):13375).

Instead of these sums, a convenient product of these two measurements is $$e^{i\psi}AB^* = |r|^2 + |r_m|^2 e^{2i\psi} + e^{i\psi} 2 \, \text{Real}\{e^{-i\psi} r^* r_m\}$$

where * denotes complex conjugate and Real{ } denotes the real portion of a complex value. The product above has its terms nicely distinguished by the phase factors $e^{-i\psi}$. Taking the real part of $e^{i\psi}AB^*$, and then selecting the positive portions, selects the desired reflected power $|r|^2$ and suppresses the artifact terms, as seen in FIG. 11c. Preferred values for the phase shift My are between 45° and 135° so that the mirror image term $|r_m|^2 e^{2i\psi}$ has no positive real part. A phase shift near 45° has the advantage that the mirror image term is imaginary, so that it neither adds nor subtracts to the real-valued upright image.

Another method to sufficiently disambiguate the upright and mirror images is by comparing two images taken with slightly different settings of the patient position, or preferably slightly different positions of the reference path length. Recent advances in sub-image tracking algorithms, driven by the need for compression of digital video, provide a choice of method to separate the two image components.

It is possible to generate a pair of images at different apparent patient positions with only one OCT acquisition. Chromatic dispersion of the materials in the sample and reference paths causes different wavelengths of light to have different delays (as discussed in more detail in US Patent Application Publication 20060171503). Thus OCT images formed by selecting different spectral regions of the illumination light will have different apparent distances to the patient. In spectral-domain OCT methods, the pair of images can be constructed from different spectral segments of the data recorded in a single acquisition.

Eye Length

The length to the retina must be known for intraocular lens prescription. Interferometric techniques closely related to OCT have long been used to accurately measure human eye length, such as in the commercial device IOL Master.

Figure 12:
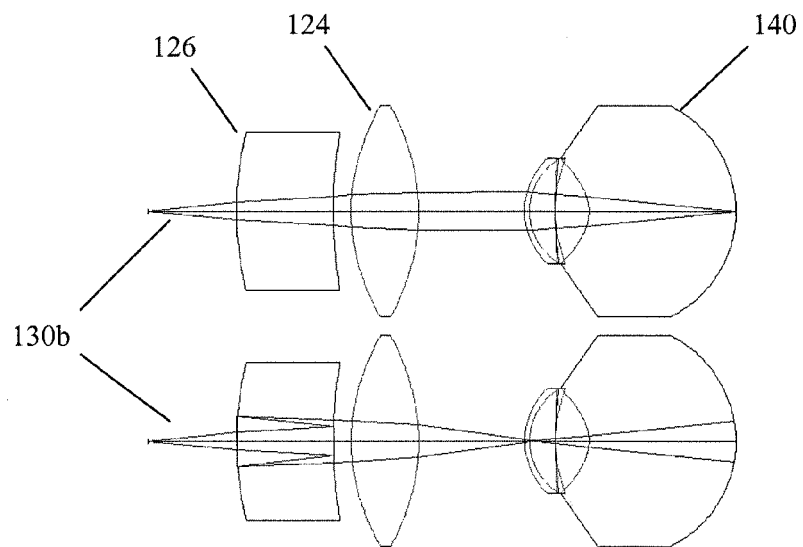
FIG. 12 is a schematic illustration of apparatus to simultaneously focus an OCT beam on the anterior and posterior sections of the human eye

Few OCT devices have the range required to image the measure the entire 25 mm depth of the human eye. Double image techniques have been described in a co-pending US patent application Ser. No. (Publication 20070076217) to either quickly switch between or simultaneously collect light from the anterior and posterior portions of the human eye. FIG. 12 shows an additional method to form a double image, in which the corneal focus is adjusted and path length compensated using a single lens. Lens 126 performs these two functions and can be removed for simple single-range imaging. The standard ophthalmic lens 124 is in the center and the patient's eye 140 is represented at right. The rays in OCT beam 130b are split by partial reflection into rays that focus on the retina and rays that focus on the cornea. The upper and lower ray diagrams show the rays retinal focus and corneal focus, respectively. These paths are active simultaneously, due to partial reflection at the lens surfaces. The double reflection preferably adds optical path length close to that of a 25-mm-long typical human eye. The glass of the lens will probably not compensate for the chromatic dispersion in the eye, but this can be advantageous because from a single acquisition one can choose to numerically correct for dispersion to make sharp either the retinal image or the corneal image. The lens is shown just behind the ophthalmic lens for compact illustration, but it could be anywhere along the free-space path of the OCT beam if the lens is near the fiber collimator, at which location the beam is not moved by the scanner, a selective-area reflective coating could be applied to enhance the efficiency of the corneal-focus path.

Using a retinal SD-OCT scanner, with single-sided depth range 3 mm in tissue, and applying the techniques above to distinguish upright from mirror image, one can fit both retina and cornea on the same image for a range of eye lengths from 19 mm to 31 mm. If the eye is 19 mm long, the retina appears in the extreme top of the image, 3 mm above the reference depth, and the cornea appears at the extreme bottom of the image, 3 mm below the reference depth. If the eye is 31 mm long, the retina appears in the extreme bottom of the image, 3 mm below the reference depth, and the cornea appears at the extreme top of the image, 3 mm above the reference depth.

Although various embodiments that incorporate the teachings of the present invention have been shown and described in detail herein, those skilled in the art can readily devise many other varied embodiments that still incorporate these teachings.

The following are incorporated herein by reference.

US Patent Documents
  U.S. Pat. No. 6,377,349 Fercher
  U.S. Pat. No. 6,788,421 Fercher
  U.S. Pat. No. 5,317,389 Hochberg
  U.S. Pat. No. 6,282,011 Tearney
  U.S. Pat. No. 6,549,801 Chen
  U.S. Pat. No. 6,735,463 Izatt
  U.S. Pat. No. 6,741,359 Wei
  U.S. Pat. No. 7,452,077 Meyer
  US Publication 2005/0140981 Waelti
  US Publication 2005/0203422 Wei
  US Publication 2006/0072424 Everett
  US Publication 2006/0228011 Everett
  US Publication 2006/0171503 O'Hara
  US Publication 2006/0256343 Choma
  US Publication 2007/0076217 Baker Other Publications
  Huang *Lasers and Surgery in Medicine* 11: 419-425 (1991)
  Podoleanu *Optics Letters* 23(3): 147-149 (1998)
  Holladay *Operative Techniques in Cataract and Refractive Surgery* 1(3):105 (1998)
  Zhao *Optics Letters* 25(2): 114-116(2000)
  Leitgeb *Optics Express* 11(23): 3116-3121 (2003)
  Park *Optics Express* 13(11): 3931-3944 (2005)
  Baikoff *Journal of Cataract & Refractive Surgery* 30(9): 1843-1850 (2004)
  Vakoc *Optics Express* 13(14):5483 (2005)
  Yasuno *Applied Optics* 45(8):1861 (2006)
  Tang *Journal of Cataract & Refractive Surgery* 32: 1843-1850 (2006).
  Baumann *Optics Express* 15(20):13375 (2007)

We claim:

1. A method for determining the shape of the front surface of the cornea using an optical coherence tomography (OCT)

system, the OCT system including a light source generating a light beam, a sample arm, a reference arm and a detection arm, the method comprising the steps of:

scanning the eye with the light beam;

simultaneously collecting light specularly reflected from the anterior surface of the cornea and diffusely reflected light from interior portions of the cornea and interfering the collected light with light from the reference arm and generating output signals in response to the interfered light, said collecting step being performed at a plurality of light beam scan positions;

processing the output signals corresponding to the specularly reflected light to determine the shape of the anterior corneal surface, and processing the output signals corresponding to the diffusely reflected light to determine the shape of the posterior corneal surface and wherein the processing of the output signals corresponding to the specularly reflected light to determine the shape of the anterior corneal surface includes an adjustment to correct for an apparent displacement of the anterior corneal surface said adjustment being based on the slope of the anterior corneal surface with respect to the light beam; and displaying the results.

2. A method as recited in claim 1, wherein the scanning is performed so that light specularly reflected from the anterior surface is collected over at least 3 mm transverse extent on the cornea.

3. A method as recited in claim 1, wherein said step of processing the output signals to determine the shape of the anterior corneal surface comprises deriving changes in phase of the specularly reflected light as a function of scan position.

4. A method as recited in claim 1, wherein said step of processing the output signals to determine the shape of the anterior corneal surface comprises determining the peak of intensity along the propagation axis of the specularly reflected light as a function of scan position.

5. A method as recited in claim 1, further including a step of determining a refractive power of the cornea based on the determined shapes of the anterior and posterior corneal surfaces.

6. A method as recited in claim 1, wherein during said processing step, artifacts in the output signals due to movement of the eye during scanning are corrected.

7. A method as recited in claim 6, wherein the effects of movement of the eye are at least partially corrected by deriving Doppler shift information from the output signals.

8. A method as recited in claim 7, wherein the Doppler shift information is based on the collected diffusely reflected light.

9. A method as recited in claim 1, wherein during the processing step, a tomogram image is generated from the specularly and diffusely reflected light and the tomogram image is further processed to derive the shape of the anterior corneal surface.

10. An optical coherence tomography (OCT) system, the OCT system including a light source generating a light beam, a sample arm, a reference arm, and a detection arm, said OCT system comprising:

optics for scanning the light beam over the cornea in a manner so that both light specularly reflected from the anterior surface of the cornea and light diffusely reflected light from interior portions of the cornea are simultaneously collected via the detection arm and interfered with light from the reference arm;

a detector coupled to the detection arm for generating output signals in response to the interfered light; and a processor receiving the output signals and determining the shape of the anterior corneal surface, based on the output signals corresponding to the specularly reflected light and wherein the shape of the posterior corneal surface is determined based on the output signals corresponding to the diffusely reflected light and wherein the determination of the shape of the anterior corneal surface includes an adjustment to correct for an apparent displacement of the anterior corneal surface, said adjustment being based on the slope of the anterior corneal surface with respect to the light beam.

11. A system as recited in claim 10, wherein the scanning optics functions to maintain the beam at substantially normal incidence with respect to the anterior surface of the cornea during the scanning step.

12. A system as recited in claim 10, wherein said processor determines the shape of the anterior corneal surface by first generating a tomogram image of the cornea from the specularly and diffusely reflected light.

13. A system as recited in claim 10, wherein the scanning optics are arranged so that the specularly reflected light from the anterior surface is collected over at least 3 mm transverse extent on the cornea.

14. A system as recited in claim 10, wherein said processor determines the shape of the anterior corneal surface by deriving changes in phase of the specularly reflected light as a function of scan position.

15. A system as recited in claim 10, wherein said processor determines the shape of the anterior corneal surface by determining the peak of intensity along the z-axis of the specularly reflected light as a function of scan position.

16. A system as recited in claim 10, wherein the processor determines a refractive power of the cornea based on the determined shapes of the anterior and posterior corneal surfaces.

17. A system as recited in claim 10, wherein the processor corrects for artifacts in the output signals due to movement of the eye during scanning.

18. A system as recited in claim 17, wherein the effects of movement of the eye are at least partially corrected by deriving Doppler shift information from the output signals.

19. A method as recited in claim 18, wherein the Doppler shift information is based on the collected diffusely reflected light.

20. A method of generating tomographic images using an optical coherence tomography (OCT) system, the OCT system including a light source generating a light beam, a sample arm, and a reference arm, the method comprising the steps of:

transversely moving the light beam with respect to a sample and collecting the light reflected therefrom;

interfering the collected light with light from the reference arm and generating output signals in response to the interfered light;

generating a tomogram based on the output signals;

analyzing the variations in speckle in the tomogram in order to determine the speed of the transverse motion of the light beam with respect to the sample;

generating a tomographic image from the output signals based on the determined speed of the transverse motion; and displaying the image.

21. A method as recited in claim 20, wherein the output signals correspond to a sequence of axial scans and variations in the speckle are analyzed by measuring a cross correlation between successively collected axial scans.

22. A method as recited in claim 20 wherein the sample arm includes a hand held probe for directing the light beam and wherein the step of transversely moving the light beam with respect to the sample is performed by moving the probe by hand.

23. A method as recited in claim 20 wherein the sample arm includes optics for scanning the light beam with respect to the sample.

24. A method for determining the shape of the front surface of the cornea using an optical coherence tomography (OCT) system, the OCT system including a light source generating a light beam, a sample arm, a reference arm and a detection arm, the method comprising the steps of:

scanning the eye with the light beam;

simultaneously collecting light specularly reflected from the anterior surface of the cornea and diffusely reflected light from interior portions of the cornea and interfering the collected light with light from the reference arm and generating output signals in response to the interfered light, said collecting step being performed at a plurality of light beam scan positions;

processing the output signals corresponding to the specularly reflected light to determine the shape of the anterior corneal surface, and processing the output signals corresponding to the diffusely reflected light to determine the shape of the posterior corneal surface and wherein the processing of the output signals corresponding to the specularly reflected light to determine the shape of the anterior corneal surface includes deriving changes in phase of the specularly reflected light as a function of scan position; and displaying the results.

25. A method as recited in claim 24, wherein the scanning is performed so that the light specularly reflected from the anterior surface is collected over at least 3 mm transverse extent on the cornea.

26. A method as recited in claim 24, wherein during the processing step, artifacts in the output signals due to movement of the eye during scanning are at least partially corrected using Doppler shift information derived from the output signals.

27. An optical coherence tomography (OCT) system, the OCT system including a light source generating a light beam, a sample arm, a reference arm, and a detection arm, said OCT system comprising:

optics for scanning the light beam over the cornea in a manner so that both light specularly reflected from the anterior surface of the cornea and light diffusely reflected light from interior portions of the cornea are simultaneously collected and interfered with light from the reference arm;

a detector coupled to the detection arm for generating output signals in response to the interfered light; and a processor receiving the output signals and determining the shape of the anterior corneal surface, based on the specularly reflected light and wherein the shape of the shape of the posterior corneal surface is determined based on the diffusely reflected light and wherein the determination of the shape of the anterior corneal surface includes deriving changes in phase of the specularly reflected light as a function of scan position; and wherein the scanning optics are arranged so that the light specularly reflected from the anterior surface is collected over at least 3 mm transverse extent on the cornea.

28. An apparatus as recited in claim 27 wherein the processor corrects artifacts in the output signals due to movement of the eye during scanning using Doppler shift information derived from the output signals.

* * * * *

UNITED STATES PATENT AND TRADEMARK OFFICE
CERTIFICATE OF CORRECTION

PATENT NO. : 7,878,651 B2
APPLICATION NO. : 12/336252
DATED : February 1, 2011
INVENTOR(S) : Keith E. O'Hara et al.

Page 1 of 1

It is certified that error appears in the above-identified patent and that said Letters Patent is hereby corrected as shown below:

In column 2, line 20, delete "motion" and insert -- motion. --, therefor.

In column 2, line 29, delete "eye" and insert -- eye. --, therefor.

In column 6, line 45, delete "(t,u)" and insert -- (t, u) --, therefor.

In column 12, line 61, delete "v" and insert -- $\psi$ --, therefor.

In column 13, line 25, delete "My" and insert -- $\psi$ --, therefor.

In column 18, line 20-21, in claim 27, after "of" delete "the shape of".

Signed and Sealed this
Seventeenth Day of May, 2011

David J. Kappos
*Director of the United States Patent and Trademark Office*